United States Patent
Mertens et al.

(10) Patent No.: US 7,544,851 B2
(45) Date of Patent: Jun. 9, 2009

(54) METHOD OF SYNTHESIZING ALUMINOPHOSPHATE AND SILICOALUMINOPHOSPHATE MOLECULAR SIEVES

(75) Inventors: Machteld Maria Mertens, Boortmeerbeek (BE); Thomas H. Colle, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/715,163

(22) Filed: Mar. 7, 2007

(65) Prior Publication Data

US 2007/0249492 A1    Oct. 25, 2007

Related U.S. Application Data

(60) Provisional application No. 60/794,863, filed on Apr. 25, 2006, provisional application No. 60/794,622, filed on Apr. 25, 2006, provisional application No. 60/845,096, filed on Sep. 15, 2006.

(51) Int. Cl.
   *C07C 1/20*    (2006.01)
(52) U.S. Cl. .................. 585/640; 585/324; 585/326; 585/327; 585/329; 585/638; 585/639
(58) Field of Classification Search ............ 585/324, 585/326, 327, 329, 638, 639, 640
   See application file for complete search history.

(56) References Cited

U.S. PATENT DOCUMENTS

| | | | |
|---|---|---|---|
| 4,499,327 A | 2/1985 | Kaiser | |
| 5,126,308 A | 6/1992 | Barger et al. | |
| 5,609,843 A | 3/1997 | Wendelbo | |
| 5,879,655 A | 3/1999 | Miller et al. | |
| 6,334,994 B1 | 1/2002 | Wendelbo et al. | |
| 6,812,372 B2 | 11/2004 | Janssen et al. | |
| 6,838,586 B2 * | 1/2005 | Mertens et al. | 585/640 |
| 6,953,767 B2 | 10/2005 | Janssen et al. | |
| 7,090,814 B2 | 8/2006 | Mertens et al. | |

FOREIGN PATENT DOCUMENTS

| WO | WO 02/070407 | 9/2002 |
|---|---|---|
| WO | WO 2006/052883 | 5/2006 |

OTHER PUBLICATIONS

H. van Bekkum et al., Studies in Surface Science and Catalysis, vol. 137, Elsevier Science, 2001, pp. 1-67.

* cited by examiner

*Primary Examiner*—Elizabeth D Wood

(57) ABSTRACT

In a method of synthesizing an aluminophosphate or silicoaluminophosphate molecular sieve, a synthesis mixture is prepared by mixing a plurality of starting materials including at least a source of water, a source of phosphorus, a source of aluminum, optionally, a source of silicon and, and at least one organic directing agent for directing the formation of said molecular sieve. The starting materials are maintained at a temperature between 25° C. and 50° C., preferably between 30° C. and 45° C., during the mixing and until preparation of the starting mixture is complete, whereafter the synthesis mixture is heated to a crystallization temperature between about 100° C. and about 350° C. until crystals of the molecular sieve are produced. When crystallization is complete, the molecular sieve is recovered.

4 Claims, 4 Drawing Sheets

METHOD OF SYNTHESIZING ALUMINOPHOSPHATE AND SILICOALUMINOPHOSPHATE MOLECULAR SIEVES

CROSS REFERENCE TO RELATED APPLICATIONS

This application claims the benefit of and priority from U.S. Ser. No. 60/794,863, filed Apr. 25, 2006, U.S. Ser. No. 60/794,622, filed Apr. 25, 2006, and U.S. Ser. No. 60/845,096, filed Sep. 15, 2006. The above applications are fully incorporated herein by reference.

FIELD OF THE INVENTION

This invention relates to a method of synthesizing aluminophosphate and silicoaluminophosphate molecular sieves and to the use of the resultant molecular sieves as catalysts for the conversion of oxygenates, particularly methanol-to-olefins, particularly ethylene and propylene.

BACKGROUND OF THE INVENTION

Light olefins, such as ethylene, propylene, butylenes, and mixtures thereof, serve as feeds for the production of numerous important chemicals and polymers. Typically, $C_2$-$C_4$ light olefins are produced by cracking petroleum refinery streams, such as $C_3$+ paraffinic feeds. In view of limited supply of competitive petroleum feeds, production of low cost light olefins from petroleum feeds is subject to waning supplies. Efforts to develop light olefin production technologies based on alternative feeds have therefore increased.

An important type of alternative feed for the production of light olefins is oxygenates, such as $C_1$-$C_4$ alkanols, especially methanol and ethanol; $C_2$-$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastic, municipal waste, or any organic material. Because of the wide variety of sources, alcohol, alcohol derivatives, and other oxygenates have promise as economical, non-petroleum sources for light olefin production.

The preferred process for converting an oxygenate feedstock, such as methanol, into one or more olefin(s), primarily ethylene and/or propylene, involves contacting the feedstock with a crystalline molecular sieve catalyst composition. Crystalline molecular sieves all have a three-dimensional, four-connected framework structure of corner-sharing [TO4] tetrahedra, where T is one or more tetrahedrally coordinated cations. Examples of well known molecular sieves are silicates, which comprise [SiO4] tetrahedral units; aluminosilicates, which comprise [SiO4] and [AlO4] tetrahedral units; aluminophosphates, which comprise [AlO4] and [PO4] tetrahedral units; and silicoaluminophosphates, which comprise [SiO4], [AlO4], and [PO4] tetrahedral units.

Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pp. 1-67, Elsevier Science, B.V., Amsterdam, Netherlands (2001). Among the molecular sieves that have been investigated for use as oxygenate conversion catalysts, small pore aluminophosphates and silicoaluminophosphates (having a pore size less than 5 Å), such as SAPO-34, have shown particular promise. SAPO-34 belongs to the family of molecular sieves having the framework type of the zeolitic mineral chabazite (CHA).

Also reported as having activity in the conversion of oxygenates to olefins are intergrowths of CHA framework-type molecular sieves with AEI framework type molecular sieves, such as RUW-19 as disclosed in U.S. Pat. No. 6,334,994 and EMM-2 as disclosed in U.S. Pat. Nos. 6,812,372 and 6,953,767.

For example, U.S. Pat. No. 4,499,327 discloses a process of making light olefins containing 2 to 4 carbon atoms which comprises contacting a feedstock comprising one or more of methanol, ethanol, dimethyl ether, diethyl ether and mixtures thereof with a silicoaluminophosphate (SAPO) molecular sieve having a specified unit empirical formula in the as-synthesized and anhydrous form. Preferred SAPOs are those that have pores large enough to adsorb xenon (kinetic diameter of 4.0 Å), but small enough to exclude isobutane (kinetic diameter of 5.0 Å), with SAPO-34 being particularly preferred.

In addition to framework topology, one of the factors that frequently affects the efficacy of a molecular sieve for use in the conversion of oxygenates-to-olefins is the crystal size and crystal size distribution of the molecular sieve particles. For example, U.S. Pat. No. 5,126,308 reports that an aluminophosphate catalyst having the formula $(EL_xAl_yP_z)O_2$, wherein EL is a metal selected from the group consisting of silicon, magnesium, zinc, iron, cobalt, nickel, manganese, chromium, and mixtures thereof, has improved catalyst life and decreased by-product formation in oxygenate conversion reactions when at least 50% of the catalyst particles have a particle size smaller than 1.0 µm and no more than 10% of the particles have particle sizes greater than 2.0 µm. In particular, the Examples of the '308 patent show that SAPO-34 having a median particle diameter, expressed as a mass distribution, of 0.71 micrometers and 90% of the total sample mass having a median particle diameter <1.2 micrometers had a longer life and produced less $C_3$ by-product in methanol conversion than SAPO-34 having a median particle diameter of 0.90 micrometers, 90% of the total sample mass having a median particle diameter <3.0 micrometers and 10% having a median particle size <0.5 micrometers.

The synthesis of aluminophosphate and silicoaluminophosphate molecular sieves involves preparing a reaction mixture by mixing a variety of starting materials including a source of water, a source of phosphorus, a source of aluminum, optionally, a source of silicon, and at least one organic directing agent for directing the formation of the desired molecular sieve. The resultant mixture is then heated, normally with agitation, to a suitable crystallization temperature, typically between about 100° C. and about 300° C., and then held at this temperature for a sufficient time, typically between about 1 hour and 20 days, for crystallization of the desired molecular sieve to occur.

According to the present invention, it has now been found that controlling the temperature during mixing of the starting materials and, in particular, ensuring that the temperature of the starting materials is kept between 25° C. and 50° C., preferably between 30° C. and 45° C., until formation of the reaction mixture is complete, is important in synthesizing aluminophosphate and silicoaluminophosphate molecular sieves having a homogeneous crystal size distribution. One way of measuring the homogeneity of crystal size distribution is by determining crystal size span, wherein the crystal size span is defined as:

$$(d90-d10)/d50$$

where d10, d50, and d90 are the maximum particle sizes of 10%, 50%, and 90% respectively of the molecular sieve particles. In particular, it is found that by maintaining the temperature between 25° C. and 50° C., preferably between 30° C. and 45° C., until gel formation is complete it is possible to produce CHA framework-type aluminophosphate and silicoaluminophosphate molecular sieves in which the crystal size span is less than 1.

In our issued, commonly assigned U.S. Pat. No. 7,090,814, we have disclosed a method of synthesizing a novel silicoaluminophosphate molecular sieve, in which a synthesis mixture is prepared by combining a source of phosphorus and at least one organic directing agent; and then the combination of the phosphorus source and organic directing agent is cooled to a temperature of less than or equal to 50° C., preferably less than or equal to 30° C., prior to introducing a source of aluminum into the combination. After addition of a source of silicon, the synthesis mixture is heated to a crystallization temperature of between about 100° C. and about 300° C. and the molecular sieve is recovered.

SUMMARY OF THE INVENTION

In one aspect, the invention resides in a method of synthesizing an aluminophosphate or silicoaluminophosphate molecular sieve, the method comprising:

(a) mixing a plurality of starting materials to prepare a synthesis mixture, the starting materials including at least a source of water, a source of phosphorus, a source of aluminum, optionally, a source of silicon, and at least one organic directing agent for directing the formation of said molecular sieve;

(b) maintaining said starting materials at a temperature between 25° C. and 50° C. during the mixing (a) and until preparation of the starting mixture is complete;

(c) heating said synthesis mixture to a crystallization temperature between about 100° C. and about 350° C. until crystals of said molecular sieve are produced; and (d) recovering said molecular sieve crystals.

Conveniently, the starting materials are maintained at a temperature between 30° C. and 45° C. until preparation of the starting mixture is complete.

Conveniently, the crystallization temperature is between about 125° C. and about 270° C.

Typically, the particle size distribution of the molecular sieve crystals is such that the (d90–d10)/d50 ratio of the particles is smaller than the particle size distribution that would be obtained by allowing the temperature to drop below 25° C. or to exceed 50° C. during the mixing (a) and preferably said ratio is less than 1. Conveniently, the molecular sieve crystals have an average, d50, particle size of less than 3 microns.

Conveniently, said aluminophosphate or silicoaluminophosphate comprises a CHA framework-type molecular sieve.

In a further aspect, the invention resides in a crystalline aluminophosphate or silicoaluminophosphate molecular sieve comprising a CHA framework-type material and having a particle size distribution such that the (d90–d10)/d50 ratio is less than 1.

Preferably, the crystals of the molecular sieve have an average, d50, particle size of less than 3 microns.

DETAILED DESCRIPTION OF THE INVENTION

Figure 1:
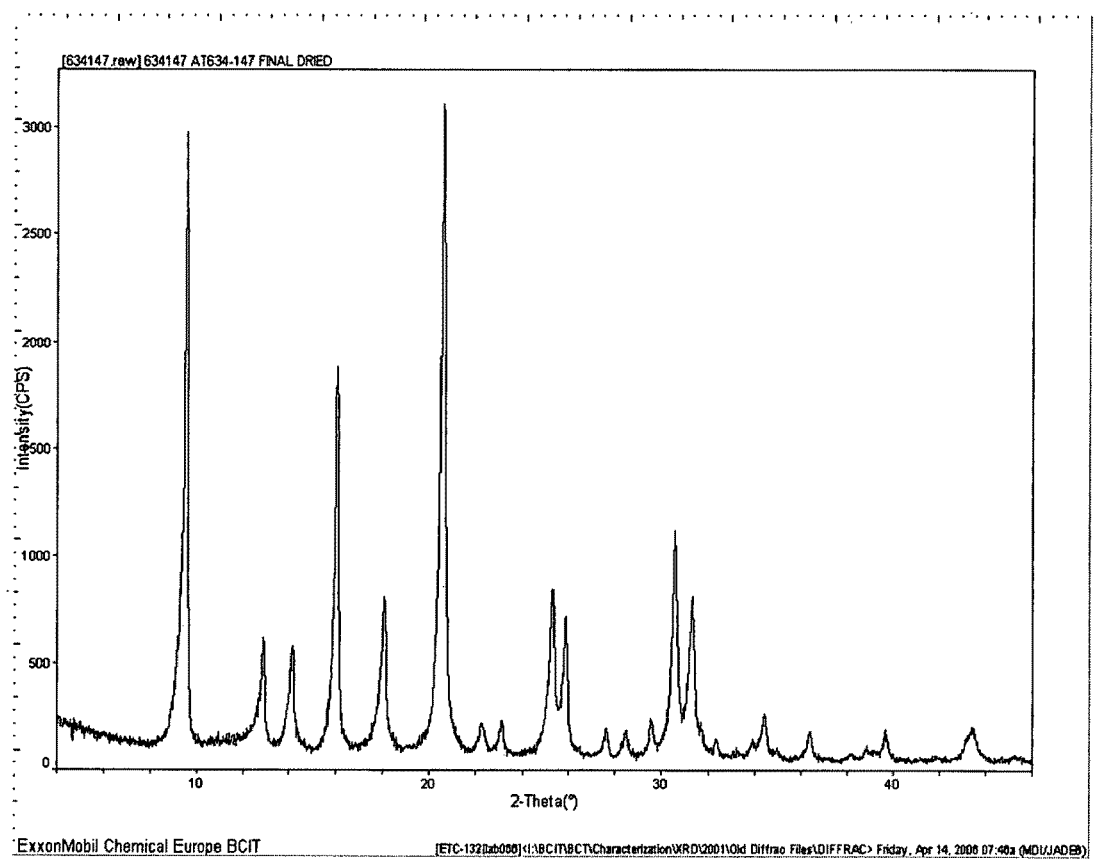
FIG. 1 is an X-ray diffraction pattern of the product of Example 1.

As used herein, the reference to the "dx" particle size of a molecular sieve means that x percent by volume of a specified plurality of particles of the molecular sieve have a particle diameter no greater than the cited particle size. For example, the d50 value for a specified plurality of particles means that 50% by volume of the particles have a particle diameter no greater than the cited d50 value. The d50 value is also referred to as the average or median particle diameter. For the purposes of this definition, the particle size distribution (PSD) used to define the dx value is measured using well known laser scattering techniques using a Malvern Mastersizer Model 2000 from Malvern Instruments Limited. "Particle diameter" as used herein means the diameter of a specified spherical particle or the equivalent diameter of non-spherical particles as measured by laser scattering using a Malvern Mastersizer Model 2000 particle size analyzer.

The present invention is directed to a method of synthesizing an aluminophosphate or silicoaluminophosphate molecular sieve by mixing water with a source of phosphorus, a source of aluminum, optionally, a source of silicon, and at least one organic directing agent to form a synthesis mixture and then heating the synthesis mixture to a temperature between about 100° C. and about 350° C. until crystals of the molecular sieve are produced. The present method is based on the unexpected finding that by maintaining the temperature of the starting materials used to from the synthesis mixture between 25° C. and 50° C., preferably between 30° C. and 45° C., during the entire mixing operation, the particle size and the particle size distribution of the resultant molecular sieve is reduced. In particular, it is possible to produce aluminophosphate and silicoaluminophosphate molecular sieves, in which the average, d50, particle size is less than 3 microns and the (d90–d10)/d50 is less than 1.

The molecular sieves produced by the present process are useful as adsorbents and in the conversion of an oxygenate-containing feedstock, such as methanol, to a product comprising olefins, such as ethylene and propylene or alkylamines.

Molecular Sieves

Crystalline molecular sieves have a three-dimensional, four-connected framework structure of corner-sharing [$TO_4$] tetrahedra, where T is any tetrahedrally coordinated cation. In the case of aluminophosphates (AlPOs), the framework structure is composed of [$AlO_4$] and [$PO_4$] tetrahedral units, whereas in the case of silicoaluminophosphates (SAPOs), the framework structure is composed of [$SiO_4$], [$AlO_4$], and [$PO_4$] corner sharing tetrahedral units. The molecular sieves produced by the present process are aluminophosphates and silicoaluminophosphates although additional metal oxide

[MeO4] units can also be present, where, for example, Me is magnesium, zinc, iron, cobalt, nickel, manganese, chromium, and mixtures thereof.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types*, 5th edition, Elsevier, London, England (2001), which is fully incorporated herein by reference.

Non-limiting examples of the molecular sieves for which a structure has been established include the small pore molecular sieves of a framework type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework type selected from the group consisting of AFO, AEL, EUO, HEU, FER, MEL, MFI, MTW, MTT, TON, and substituted forms thereof; and the large pore molecular sieves of a framework type selected from the group consisting of EMT, FAU, and substituted forms thereof. Other molecular sieves have a framework type selected from the group consisting of ANA, BEA, CFI, CLO, DON, GIS, LTL, MER, MOR, MWW, and SOD. Also known are molecular sieves that comprise intergrowths of two or more framework topologies.

Non-limiting examples of the preferred molecular sieves, particularly for converting an oxygenate-containing feedstock into olefin(s), include those having a framework type selected from the group consisting of AEL, AFY, BEA, CHA, EDI, FAU, FER, GIS, LTA, LTL, MER, MFI, MOR, MTT, MWW, TAM, and TON.

Molecular sieves are typically described in terms of the size of the ring that defines a pore, where the size is based on the number of T atoms in the ring. Small pore molecular sieves generally have up to 8-ring structures and an average pore size less than 5 Å, whereas medium pore molecular sieves generally have 10-ring structures and an average pore size of about 5 Å to about 6 Å. Large pore molecular sieves generally have at least 12-ring structures and an average pore size greater than about 6 Å. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pp. 1-67, Elsevier Science, B.V., Amsterdam, Netherlands (2001).

Conveniently, the molecular sieve produced by the method of the invention is a small pore aluminophosphate or silicoaluminophosphate material having a CHA topology, particularly SAPO-34.

Molecular Sieve Synthesis

Generally, molecular sieves are synthesized by the hydrothermal crystallization of a synthesis mixture comprising water, sources of one or more of silicon, aluminum, and phosphorus, and at least one organic directing agent for directing the formation of said molecular sieve. Typically, the synthesis mixture, optionally, together with seeds from another or the same framework-type molecular sieve, is placed in a sealed pressure vessel, optionally, lined with an inert plastic such as polytetrafluoroethylene, and heated, under a crystallization pressure and temperature, until a crystalline material is formed, and then recovered by filtration, centrifugation, and/or decanting.

Non-limiting examples of suitable silicon sources include silicates, fumed silica, for example, those sold under the trade names Ultrasil, Hisil, Aerosil-200 available from Degussa Inc., New York, N.Y., and CAB-O-SIL M-5, precipitated silica, e.g., that sold under the name Baker's silica, organosilicon compounds such as tetraalkyl orthosilicates, for example, tetramethyl orthosilicate (TMOS) and tetraethylorthosilicate (TEOS), colloidal silicas or aqueous suspensions thereof, for example, Ludox AS-40 and HS-40 sols available from E.I. du Pont de Nemours, Wilmington, Del., silicic acid, or any combination thereof.

Non-limiting examples of suitable aluminum sources include organoaluminum compounds such as aluminum alkoxides, for example aluminum isopropoxide, and inorganic aluminum sources, such as alumina, alumina hydrate, alumina sols, aluminum phosphate, aluminum hydroxide, sodium aluminate, aluminum trichloride, gibbsite, and pseudo-boehmite, e.g. that sold under the trade names Pural SB, Catapal, Disperal, and Versal, or any combination thereof. Preferred sources are inorganic aluminum compounds, such as hydrated aluminum oxides and particularly boehmite and pseudoboehmite.

Non-limiting examples of suitable phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A preferred source of phosphorus is phosphoric acid.

The organic directing agent(s) employed in the synthesis will depend on the particular framework-type molecular sieve to be produced. However, in the case of CHA framework-type materials, such as SAPO-34, suitable directing agents include adamantammonium compounds, such as N,N,N-trimethyl-1-adamantammonium compounds, N,N,N-trimethyl-2-adamantammonium compounds, and N,N,N-trimethylcyclohexylammonium compounds, N,N-dimethyl-3,3-dimethylpiperidinium compounds, N,N-methylethyl-3,3-dimethylpiperidinium compounds, N,N-dimethyl-2-methylpiperidinium compounds, 1,3,3,6,6-pentamethyl-6-azonio-bicyclo(3.2.1)octane compounds, N,N-dimethylcyclohexylamine, and the bi- and tri-cyclic nitrogen containing organic compounds cited in (1) *Zeolites and Related Microporous Materials*: State of the Art 1994, Studies of Surface Science and Catalysis, Vol. 84, pp. 29-36; (2) *Novel Materials in Heterogeneous Catalysis* (ed. Terry K. Baker & Larry L. Murrell), Chapter 2, pp. 14-24, May 1990, (3) J. Am. Chem. Soc., 2000, 122, pp. 263-273, and (4) in U.S. Pat. Nos. 4,544,538 and 6,709,644.

Alternatively, the organic directing agent for producing CHA framework-type materials can be a compound having the formula:

$$R^1R^2N\text{—}R^3$$

wherein $R^1$ and $R^2$ are independently selected from the group consisting of alkyl groups having from 1 to 3 carbon atoms and hydroxyalkyl groups having from 1 to 3 carbon atoms and $R^3$ is selected from the group consisting of 4- to 8-membered cycloalkyl groups, optionally, substituted by 1 to 3 alkyl groups having from 1 to 3 carbon atoms; and 4- to 8-membered heterocyclic groups having from 1 to 3 heteroatoms, said heterocyclic groups being, optionally, substituted by 1 to 3 alkyl groups having from 1 to 3 carbon atoms and the heteroatoms in said heterocyclic groups being selected from the group consisting of O, N, and S. Preferably, the directing agent is selected from N,N-dimethylcyclohexylamine, N,N- dimethylmethyl-cyclohexylamine, N,N-dimethylcyclopentylamine, N,N-dimethylmethyl-cyclopentylamine, N,N-dimethylcycloheptylamine, N,N-dimethylmethylcycloheptylamine, and most preferably is N,N-dimethylcyclohexylamine (DMCHA).

In some cases, more than one organic directing agent may be employed. Examples of the synthesis of aluminophosphates and silicoaluminophosphates using multiple directing agents can be found in, for example, U.S. Pat. Nos. 4,440,871; 5,096,684; and 6,767,858.

Typically, where the desired molecular sieve is SAPO-34, the synthesis mixture has a molar composition within the following ranges:

$P_2O_5:Al_2O_3$ from about 0.5 to about 1.5;
$SiO_2:Al_2O_3$ from 0 to about 0.7;
$R:Al_2O_3$ from about 0.5 to about 2; and
$H_2O:Al_2O_3$ from about 30 to about 300, where R is the organic directing agent or agents.

According to the present invention, the synthesis mixture is produced by mixing the various starting materials described above, using stirring or other means of agitation, and with the mixing being controlled so that the temperature of the starting materials is kept between 25° C. and 50° C., preferably between 30° C. and 45° C., until formation of the reaction mixture is complete. It is to be appreciated that temperature control during initial gel formation is important not only in large scale pilot or commercial syntheses, but also in small scale syntheses, 2 liters or less, such as 600 milliliters or less, or even 150 milliliters or less.

Once formation of the synthesis mixture is complete, crystallization of the desired molecular sieve is typically effected by sealing the synthesis mixture in an autoclave and heating the mixture, preferably under autogenous pressure, to a temperature in the range of from 100° C. to about 350° C., for example from about 125° C. to about 270° C., such as from about 150° C. to about 200° C. The time required to form the crystalline product is usually dependent on the temperature and can vary from immediately up to several weeks. Typically, the crystallization time is from about 30 minutes to around 2 weeks, such as from about 45 minutes to about 240 hours, for example, from about 1 hour to about 120 hours. The hydrothermal crystallization may be carried out without or, more preferably, with agitation.

Preferably, the temperature of the synthesis mixture during the crystallization process, that is during heat-up to the crystallization temperature and during subsequent molecular sieve formation at the crystallization temperature, is controlled so that the temperature of the mixture during the process remains substantially constant across the mixture, without the formation of the hot spots that can readily arise where, for example, the mixture is in contact with a heated surface of the autoclave. In particular, the heating of the synthesis mixture is controlled so that if the average temperature of the synthesis mixture at a given time during heat-up and crystallization is T° C. then the temperature across the entire synthesis mixture is maintained within the range (T±5)° C., preferably within the range (T±3)° C. or even within the range (T±2)° C. In other words, the heating is controlled so that no portion of the synthesis mixture is at a temperature greater than 5° C. above or below the average temperature of the synthesis mixture. It is to be appreciated that this requirement does not mean that the temperature of the synthesis mixture must be maintained constant during the crystallization process. However, if the temperature is varied during the crystallization process, it should be varied consistently across the synthesis mixture.

The method used to achieve the required degree of temperature control is not narrowly defined and the skilled worker will be aware of a variety of methods that can be used to maintain the temperature of the synthesis mixture substantially uniform. In general, however, important factors in achieving the required temperature control include the use of heat sources that supply heat homogeneously rather than locally to the synthesis mixture, such as a convection oven or a heat transfer medium, such as oil, circulating over the external surface of the autoclave, and the provision of means for agitating the synthesis mixture.

Once the crystalline molecular sieve product is formed, usually in a slurry state, it may be recovered by any standard technique well known in the art, for example, by centrifugation or filtration. The recovered crystalline product may then be washed, such as with water, and then dried, such as in air.

By maintaining the temperature of the synthesis mixture between 25° C. and 50° C., preferably between 30° C. and 45° C., during its initial formation it is found that the crystalline product has a particle size distribution such that the span, (d90–d10)/d50, is less than would be obtained by allowing the mixture temperature to drop below 25° C. or to exceed 50° C. during the mixture preparation.

As a result of the synthesis process, the recovered crystalline product contains within its pores at least a portion of the organic directing agent(s) used in the synthesis. In a preferred embodiment, activation is performed in such a manner that the organic directing agent(s) is(are) removed from the molecular sieve, leaving active catalytic sites within the microporous channels of the molecular sieve open for contact with a feedstock. The activation process is typically accomplished by calcining, or essentially heating the molecular sieve comprising the organic directing agent at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent (s) from the intracrystalline pore system of the molecular sieve.

Molecular Sieve Catalyst Compositions

The molecular sieves and, in particular the silicoaluminophosphate molecular sieves, produced by the synthesis method of the invention are particularly intended for use as organic conversion catalysts. Before use in catalysis, the molecular sieves will normally be formulated into catalyst compositions by combination with other materials, such as binders and/or matrix materials, which provide additional hardness or catalytic activity to the finished catalyst.

Materials which can be blended with the molecular sieve can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of molecular sieve contained in the final catalyst product ranges from 10 to 90 weight percent of the total catalyst, preferably 20 to 80 weight percent of the total catalyst composition.

Use of the Molecular Sieve

The molecular sieves and, in particular, the silicoaluminophosphate molecular sieves, produced by the method of the invention are useful as catalysts in a variety of processes including cracking of, for example, a naphtha feed to light olefin(s) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a polymer product; reforming; hydrogenation; dehydrogenation; dewaxing of, for example, hydrocarbons to remove straight chain paraffins; absorption of, for example, alkyl aromatic compounds for separating out isomers thereof; alkylation of, for example, aromatic hydrocarbons such as benzene and alkyl benzene, optionally, with propylene to produce cumene or with long chain olefins; transalkylation of, for example, a combination of aromatic and polyalkylaromatic hydrocarbons; dealkylation; dehydrocyclization; disproportionation of, for example, toluene to make benzene and paraxylene; oligomerization of, for example, straight and branched chain olefin(s); the synthesis of monoalkylamines and dialkylamines from organic oxygenates, such as methanol.

Where the molecular sieve produced by the method of the invention is a small pore material (with a pore size less than 5 Å) and in particular is a CHA structure-type material, such as SAPO-34, the molecular sieve is particularly suitable as a catalyst for use in the conversion of oxygenates to olefins. As used herein, the term "oxygenates" is defined to include, but is not necessarily limited to, aliphatic alcohols, ethers, carbonyl compounds (aldehydes, ketones, carboxylic acids, carbonates, and the like), and also compounds containing heteroatoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen, and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

When used in an oxygenate conversion process, a catalyst comprising a molecular sieve produced by the present process is contacted with a feedstock comprising an organic oxygenate, optionally, with one or more diluents, in the vapor phase in a reaction zone at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example, from about 250° C. to about 800° C., including from about 250° C. to about 750° C., conveniently from about 300° C. to about 650° C., typically from about 350° C. to about 600° C., and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the oxygenate conversion process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example, in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Because the catalyst must be regenerated frequently, the reactor should allow easy removal of a portion of the catalyst to a regenerator, where the catalyst is subjected to a regeneration medium, such as a gas comprising oxygen, for example, air, to burn off coke from the catalyst, which restores the catalyst activity. The conditions of temperature, oxygen partial pressure, and residence time in the regenerator should be selected to achieve a coke content on regenerated catalyst of less than about 1 wt %. At least a portion of the regenerated catalyst should be returned to the reactor.

Using the various oxygenate feedstocks discussed above, particularly a feedstock containing methanol, a catalyst composition of the invention is effective to convert the feedstock primarily into one or more olefin(s). The olefin(s) produced typically have from 2 to 30 carbon atoms, preferably 2 to 8 carbon atoms, more preferably 2 to 6 carbon atoms, still more preferably 2 to 4 carbons atoms, and most preferably are ethylene and/or propylene. The resultant olefins can be separated from the oxygenate conversion product for sale or can be fed to a downstream process for converting the olefins to, for example, polymers.

The invention will now be more particularly described with reference to the following Examples.

In the Examples, X-ray Powder Diffractograms were recorded on a Siemens D500 diffractometer with voltage of 40 kV and current of 30 mA, using a Cu target and Nifilter (A=0.154 nm).

EXAMPLES

Example 1

A mixture with the following molar composition was prepared:

0.3SiO$_2$:Al$_2$O$_3$:P$_2$O$_5$:TEAOH:1.6DPA:52H$_2$O, using Ludox AS40 silica (supplied by Grace), phosphoric acid (85% concentration supplied by Aldrich), Condea Pural SB alumina, tetraethyl ammonium hydroxide TEAOH (35% concentration supplied by Eastern Chemical), dipropylamine DPA (supplied by Aldrich) and de-ionized water. In particular, 45.11 grams of the Condea Pural SB alumina was combined with 170.17 grams of water and the resultant slurry was stirred for 8 minutes. To this slurry was then added slowly (over a period of 10 minutes) 76.44 grams of the 85% phosphoric acid. The resultant mixture was stirred for 13 minutes, after which time the mixture was homogeneous. To this mixture was then added 14.9 grams of Ludox silica and the resulting mixture was stirred for a further 12 minutes. 139.66 grams of the TEAOH solution was then added to the mixture over a period of 9 minutes, whereafter the resultant mixture was stirred for a further 10 minutes before 101.19 grams of DPA was added. The final synthesis mixture was stirred for 12 minutes before being subjected to crystallization.

Table 1 summarizes the production of the synthesis mixture of Example 1 and indicates the temperature of the mixture at each stage in the process. From the moment the P-acid is added, the temperature of the synthesis mixtures is kept between 29° C. and 44° C.

TABLE 1

| Time cumulative [min from start] | Action | Temperature measured [° C.] |
| --- | --- | --- |
| 0 | Condea + water added to beaker | 19 |
|   | Mixing |   |
| 8 | Start adding P-acid | 19 |
| 18 | Finished adding P-acid | 32.5 |
|   | Mixing | 33.5 |
| 31 | Added Ludox at once | 32.5 |
|   | Mixing | 29 |
| 43 | Started adding TEAOH | 29 |
| 52 | All TEAOH added | 34 |
|   | Mixing | 29 |
| 62 | Added DPA at once | 44 |
| 74 | Stopped mixing | 37 |

Figure 2:
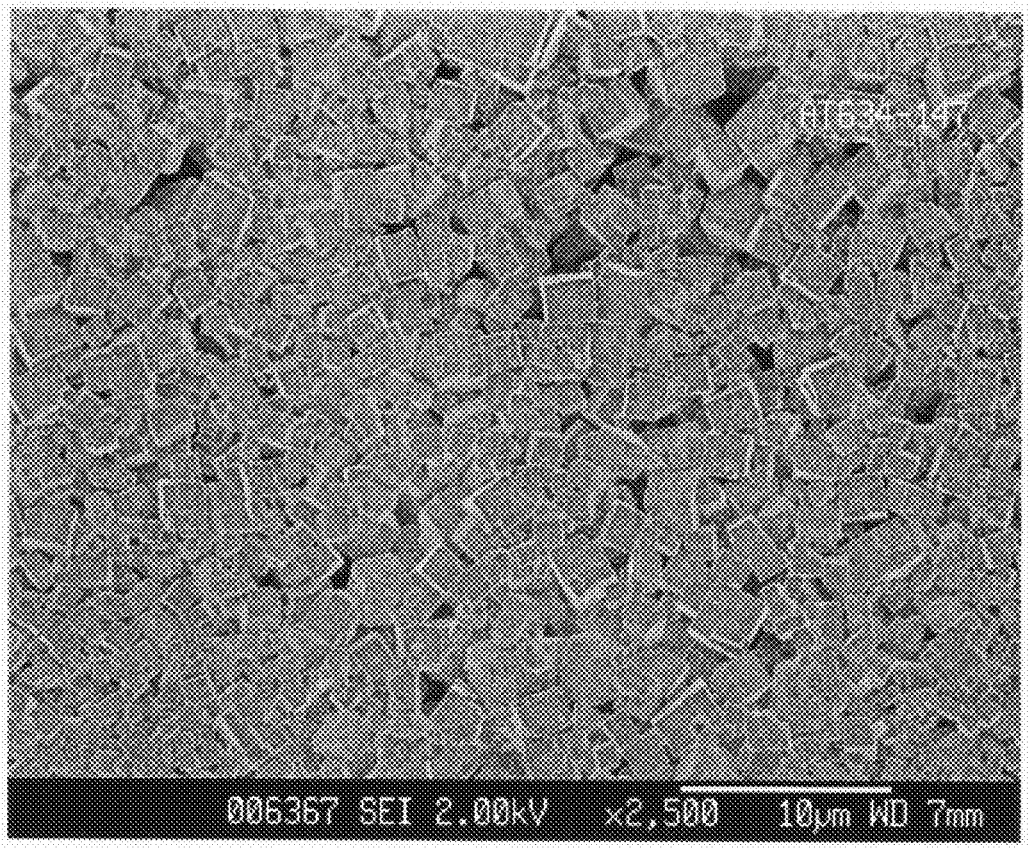
FIG. 2 is a scanning electron micrograph of the product of Example 1.

An appropriate quantity of the final synthesis mixture was transferred to a 500 milliliter autoclave resulting in a ~75% filling of the reactor volume. The autoclave was held static and was heated in 8 hours to 175° C. and then maintained at this temperature for 120 hours. After crystallization, the product was recovered by centrifuging and washing several times with de-ionized water. A portion of the resultant product was analyzed with a Malvern Mastersizer Model 2000 particle size analyzer and the remainder of the product was then dried. An XRD pattern and a scanning electron micrograph (SEM) of the dried product were recorded and the results are shown in FIGS. 1 and 2. The product was SAPO-34 having the following particle size distribution:

| d10 | 1.5 microns |
| --- | --- |
| d50 | 2.4 microns |
| d90 | 3.6 microns |
| span* | 0.9 |

*where span is (d90 − d10)/d50

Example 2

The procedure of Example 1 was repeated but with the components of the synthesis mixture being mixed in a beaker surrounded by an ice bath to retain the temperature of the mixture below 30° C. during the entire mixing process. Table 2 summarizes the production of the synthesis mixture of Example 2 and indicates the temperature of the mixture at each stage in the process. At all instances, the temperature of the synthesis mixture was at or below 28° C.

TABLE 2

| Time cumulative [min from start] | Action | Temperature measured [° C.] |
| --- | --- | --- |
| 0 | Condea + water added to beaker | 19 |
|   | Mixing/cooling | 4 |
| 8 | Start adding P-acid | 4 |
| 18 | Finished adding P-acid | 8 |
|   | mixing | 4 |
| 30 | Added Ludox at once | 4 |
|   | mixing | 3.5 |
| 43 | Started adding TEAOH | 3.5 |
| 52 | All TEAOH added | 9.5 |
|   | mixing | 10 |
| 62 | Added DPA at once | 28 |
| 74 | Stopped mixing | 11 |

Figure 3:
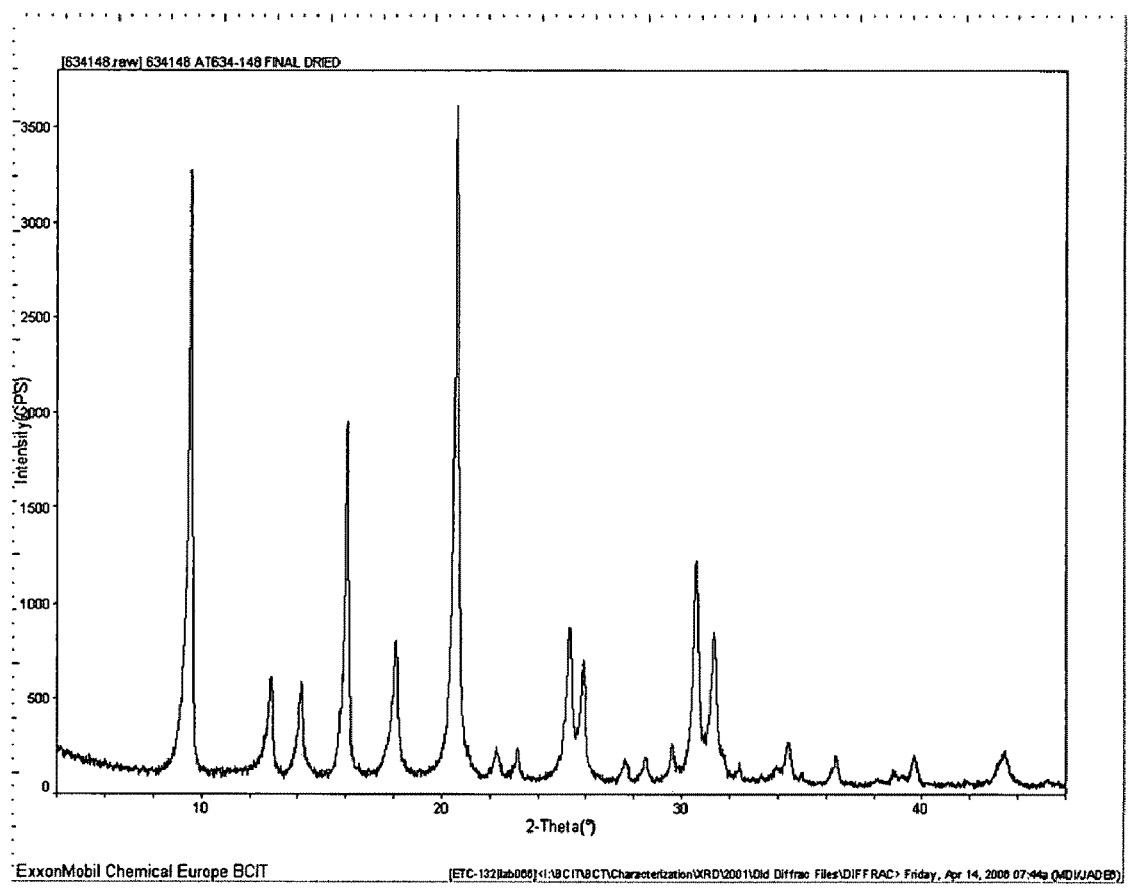
FIG. 3 is an X-ray diffraction pattern of the product of Example 2.
Figure 4:
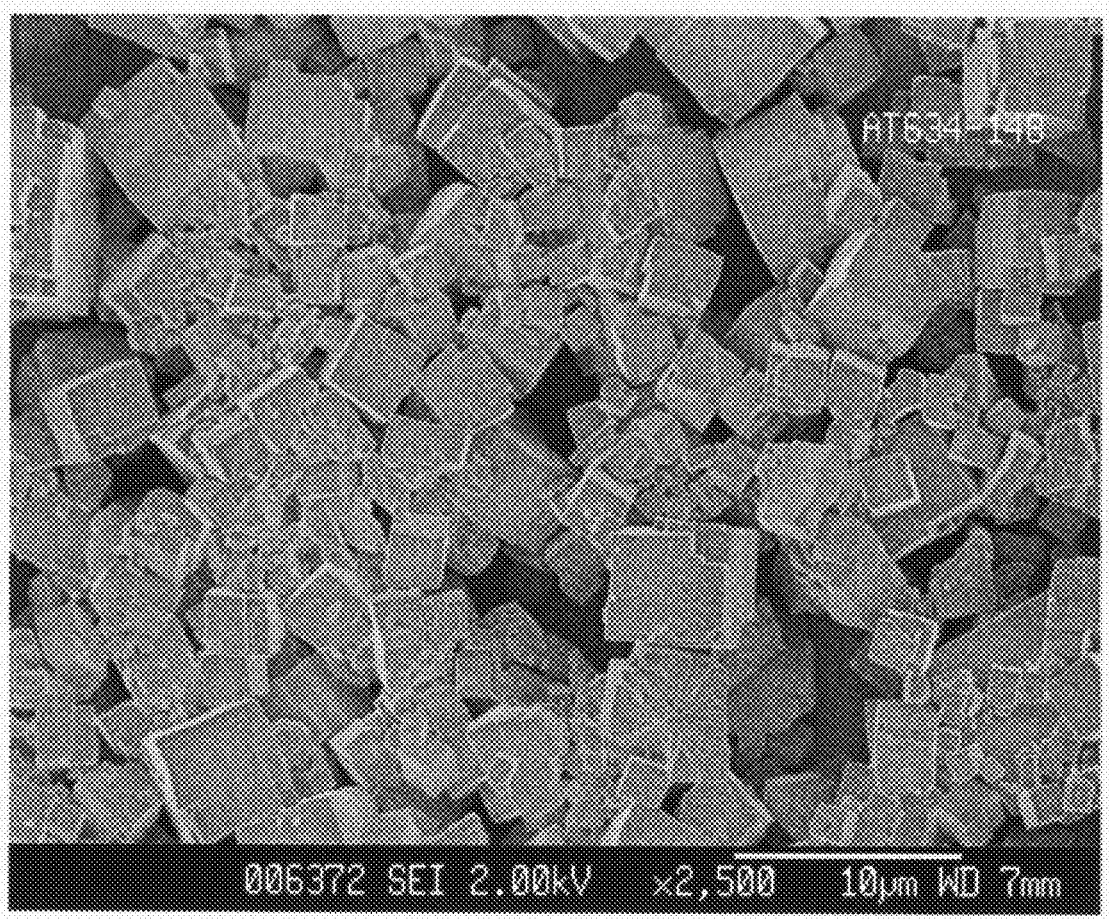
FIG. 4 is a scanning electron micrograph of the product of Example 2.

An appropriate quantity of the final synthesis mixture was transferred to a 500 milliliter autoclave resulting in a ~75% filling of the reactor volume. The autoclave was held static and was heated in 8 hours to 175° C. and then maintained at this temperature for 120 hours. After crystallization, the product was recovered by centrifuging and washing several times with de-ionized water. A portion of the resultant product was analyzed with a Malvern Mastersizer Model 2000 particle size analyzer and the remainder of the product was then dried. An XRD pattern and a scanning electron micrograph (SEM) of the dried product were recorded and the results are shown in FIGS. 3 and 4. The product was SAPO-34 having the following particle size distribution:

| d10 | 1.6 microns |
| --- | --- |
| d50 | 4.5 microns |
| d90 | 8.8 microns |
| span* | 1.6 |

*where span is (d90 − d10)/d50

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for converting an organic oxygenate starting material into a product comprising olefins or alkylamines, the process comprising contacting the starting material with a catalyst comprising a crystalline aluminophosphate or silicoaluminophosphate molecular sieve of the CHA framework-type which has a particle size distribution such that its $(d_{90}-d_{10})/d_{50}$ ratio is less than 1.

2. The process of claim 1, wherein the process comprises the conversion of aliphatic alcohols and/or ethers to olefins.

3. The process of claim 1, wherein the process comprises the conversion of an organic oxygenate to olefins and the olefins are then polymerized.

4. The process of claim 1, wherein the crystalline silicoaluminophosphate molecular sieve is synthesized by a method comprising:
  (a) (i) mixing at least a source of water and a source of aluminum with a source of phosphorus to form a synthesis mixture,
    (ii) adding a source of silicon to the synthesis mixture, and
    (iii) adding at least one organic directing agent for directing the formation of said molecular sieve to the synthesis mixture;
  (b) maintaining said synthesis mixture at a temperature between 29° C. and 44° C. from the moment the source of phosphorus is completely added into said synthesis mixture;
  (c) heating said synthesis mixture to a crystallization temperature between about 100° C. and about 350° C. until crystals of said molecular sieve are produced; and
  (d) recovering said molecular sieve crystals.

* * * * *